United States Patent [19]

Suzuki et al.

[11] Patent Number: 5,639,927
[45] Date of Patent: Jun. 17, 1997

[54] PROCESS OF PRODUCING CYCLOOLEFIN

[75] Inventors: Toshiyuki Suzuki; Tatsuya Ezaki, both of Fukuoka-ken, Japan

[73] Assignee: Mitsubishi Chemical Corporation, Japan

[21] Appl. No.: 574,025

[22] Filed: Dec. 18, 1995

[30] Foreign Application Priority Data

Dec. 19, 1994 [JP] Japan .................................. 6-315018

[51] Int. Cl.$^6$ .................. C07C 5/05; C07C 5/10; C07C 5/11

[52] U.S. Cl. .................. 585/269; 585/266; 585/271; 585/272; 585/273; 585/275; 585/277

[58] Field of Search .................. 585/266, 269, 585/271, 272, 273, 275, 277

[56] References Cited

U.S. PATENT DOCUMENTS

| | | |
|---|---|---|
| 4,197,415 | 4/1980 | Hideyuki et al. . |
| 4,575,572 | 3/1986 | Ichihashi et al. . |
| 4,665,274 | 5/1987 | Ichihashi .................. 585/267 |
| 5,157,179 | 10/1992 | Setoyama et al. . |
| 5,414,171 | 5/1995 | Richard et al. . |
| 5,457,251 | 10/1995 | Yamashita et al. .................. 585/269 |

FOREIGN PATENT DOCUMENTS

0659718A1  6/1995  European Pat. Off. .

*Primary Examiner*—Glenn A. Caldarola
*Assistant Examiner*—Elizabeth D. Wood
*Attorney, Agent, or Firm*—Nixon & Vanderhye

[57] ABSTRACT

A process of producing cycloolefin, comprises the step of subjecting a monocyclic aromatic hydrocarbon to partial hydrogenation reaction in the presence of water and a ternary catalyst containing (a) ruthenium, (b) zinc and (c) at least one selected from the group consisting of gold, silver and copper.

17 Claims, No Drawings

PROCESS OF PRODUCING CYCLOOLEFIN

BACKGROUND OF THE INVENTION

The present invention relates to a process of producing cycloolefin in which monocyclic aromatic hydrocarbon is partially hydrogenated, and more particularly to a process of producing cyclohexene comprising subjecting benzene to a partial hydrogenation reaction. The cycloolefin produced according to the present invention is useful as a raw material for lactams, dicarboxylic acid and the like which are raw materials of polyamides, or as an intermediate raw material for lysine, medicines, agricultural chemicals or the like.

It is known in the art that cycloolefin is produced by various methods such as a partial hydrogenation of monocyclic aromatic hydrocarbon, dehydration of cyclo-alkanol, dehydrogenation or oxidation-dehydrogenation of cycloalkane, or the like. Among them, if cycloolefin could be produced at high efficiency by a partial hydrogenation of a monocyclic aromatic hydrocarbon, such a method is preferred because it is a simplified reaction processes.

In the prior method in which cycloolefin is produced by partial hydrogenation of monocyclic aromatic hydrocarbon, the partial hydrogenation reaction is generally conducted in the presence of water using a catalyst composed primarily of metallic ruthenium. Many such catalysts have been proposed. For example, Japanese Patent Application Laid-open (KOKAI) Nos. 61-50,930(1986), 62-45,541(1987) and 62-45,544(1987) and U.S. Pat. No. 4,734,536 disclose methods in which the metallic ruthenium itself is used in the form of fine particles as the ruthenium-containing catalyst. Further, Japanese Patent Application Laid-open (KOKAI) Nos. 57-130,926(1982) and 61-40,226(1986) and U.S. Pat. No. 5,157,179 disclose methods in which ruthenium used is supported on a carrier such as silica, alumina, barium sulfate, zirconium silicate or the like.

It is also known in the art to use ruthenium in combination with gold, silver, copper, iron, cobalt, manganese or the like to enhance a selectivity of the cycloolefin, as disclosed in Japanese Patent Application Laid-open (KOKAI) No. 53-63,350(1978), U.S. Pat. Nos. 5,157,179 and 4,575,572. Particularly, U.S. Pat. No. 4,575,572 discloses a method in which barium sulfate is used as a carrier and three catalytically active metal components, i.e., ruthenium, either iron or cobalt, and either copper or silver are supported in combination on the carrier to obtain a ternary catalyst system.

Many of the prior procedures require the use of an additive such as a metal salt, an acid or an alkali added to the reaction system. The reason why the addition of the additive is needed, is that the reaction system without an additive disadvantageous from an industrial standpoint due to its extremely low selectivity towards the desired cycloolefin, though the reaction rate generally increases in such a reaction system using no additive.

However, when the additive such as a metal salt, etc. is added to the reaction system, the reaction system exhibits a strong corrosion property so that the attrition or deterioration of the reaction apparatus and catalyst are undesirably accelerated (Dyes and Medicines, vol. 31, No. 11, pp. 297 to 308, 1986). Because of this, further proposals have been made. For example, Japanese Patent Application Laid-open (KOKAI) No. 62-67,033(1987) discloses a method in which a nickel-coating layer is formed on a portion of a reaction vessel which comes into contact with a liquid. Japanese Patent Application Laid-open (KOKAI) No. 62-81,331 (1987) discloses a method in which a reaction vessel made of titanium or zirconium is used. In addition, Japanese Patent Application Laid-open (KOKAI) No. 6-128,177 (1994) discloses a method in which the reaction vessel made of a nickel-based alloy containing chromium and/or molybdenum is used. In these methods, the above-mentioned problem is overcome by using a generally expensive material for the reaction vessel. However, such a reaction vessel might also suffer from deficiencies such as corrosion or hydrogen embrittlement during long-term use.

As mentioned above, since the prior methods have problems or disadvantages, an industrially effective method has not necessarily been provided. For example, the known catalyst composed of multiple components still shows an unsatisfactorily low selectivity of the desired cycloolefin, or the known catalysts show only a low catalytic activity, so that cycloolefin cannot be effectively produced. Further, when additives are added to the reaction system, not only does the reaction system becomes complicated but also it is necessary to prevent the deterioration of the reaction vessel. Therefore, there is a demand for a method in which cycloolefin can be produced without addition of the additive the reaction system.

It has been found that the use of a catalyst composed of catalytically active components selected from the group consisting of specific metals and an oxide carrier supporting the catalytically active components is extremely effective for the partial hydrogenation of monocyclic aromatic hydrocarbon.

SUMMARY OF THE INVENTION

It is an object of the present invention to provide a process of producing cycloolefin in which cycloolefin can be produced by a partial hydrogenation of monocyclic aromatic hydrocarbon with high selectivity and in which cycloolefin can be produced with a high efficiency under conditions such that the attrition or deterioration of the reaction vessel and the catalyst unlikely to occur.

To accomplish this applicants provide a process of producing cycloolefin by subjecting a monocyclic aromatic hydrocarbon to partial hydrogenation in the presence of water and a ternary catalyst containing (a) ruthenium, (b) zinc and (c) at least one selected from the group consisting of gold, silver and copper.

DETAILED DESCRIPTION OF THE INVENTION:

The catalyst used in the process of the present invention is a ternary catalyst composed of (a) ruthenium, (b) zinc and (c) at least one selected from the group consisting of gold, silver and copper. Ruthenium which is the first component of the above catalyst shows catalytic activity to some extent. However, in accordance with the present invention, ruthenium as the first component of the catalyst is used in combination with the second and third components mentioned above.

An atomic ratio of zinc as the second component to ruthenium is in the range of 0.01 to 20, preferably 0.05 to 10.

In addition, the third component of the catalyst used in the process of the present invention is selected from the group consisting of gold, silver or copper all of which are elements belong to 11-group of the Periodic Table (The group number is based on IUPAC nomenclature of inorganic chemistry, revised edition (1989)). Among them, gold and copper are preferable. An atomic ratio of the third component to ruthenium is in the range of 0.01 to 20, preferably 0.03 to 10, more preferably 0.05 to 5. Examples of suitable combination of the three catalytically active components include ruthenium-zinc-gold, ruthenium-zinc-copper, or the like.

The above-mentioned catalytically active components of the present invention can be used in the form of non-carrier type particles. However, it is generally preferred that the catalytically active components are supported on a carrier, whereby an activity per the unit weight of the catalytically active components is improved and stable catalytic activity can be obtained. Examples of suitable carriers used for supporting the catalytically active components of the present invention include silica, alumina, silica-alumina, zeolite, active carbon, or generally known carriers such as a metal oxide, a composite oxide, a hydroxide, a water-insoluble metal salt and the like. Among them, water-insoluble oxides and metal salts generally used as a carrier are suitable. Specific examples of suitable carriers include a metal salt such as barium sulfate and calcium sulfate, an oxide such as silica, alumina, zirconia, titania, chromina and oxides of rare earth metals, a composite oxide such as silica-alumina, silica-zirconia and zirconium silicate, silica modified with a metal oxide such as zirconia and the like.

Among the carriers mentioned above, those exhibiting the following properties are preferably used for the purpose of the present invention. That is, when the pore distribution and the pore volume are measured using a mercury injection method, a pore volume of pores having a pore radius of 20 to 100,000 Å is in the range of 0.3 to 10 ml/g, preferably 0.5 to 5 ml/g. In addition to the above the ratio of a pore volume of the pores having a pore radius ranging from 20 to 100 Å to an entire pore volume of the carrier, is not more than 15%, preferably not more than 10%. Further, a ratio of the pore volume of the pores having a pore radius of from 100 to 100,000 Å to the entire pore volume of the carrier is not less than 85%, preferably not less than 90%. In addition, a pore volume of the pores having a pore radius of 20 to 100 Å is preferably not more than 0.2 ml/g of the carrier, particularly preferably not more than 0.15 ml/g of the carrier.

In the carriers mentioned above, generally, the oxide carrier is preferably used in the process of the present invention. Examples of the preferred oxide carrier include silica, or a silica modified with a transition metal compound. Particularly, the preferred example of the silica modified with the transition metal compound is silica modified with zirconia. The silica modified with zirconia can be generally prepared by the following method. Namely, a zirconium compound is dissolved in water or an organic solvent to prepare a solution containing zirconium compound, or an entire portion or a part of the resultant solution containing the zirconium compound is, thereafter, hydrolyzed using an alkali or the like. The thus obtained solution is impregnated into the silica using known methods such as an impregnation-applying method and a dip-coating method, followed by drying and calcining processes. Examples of the zirconium compound used in the preparation of the modified silica carrier include a zirconium halide, a zirconium oxyhalide, a zirconium nitrate, a zirconium oxynitrate, zirconium hydroxide, a complex compound such as an acetylacetonate complex of zirconium, zirconium alkoxide, or the like. The temperature used in the calcining process is a temperature at which the zirconium compound is converted to zirconia. The calcining temperature used is generally not less than 600° C., preferably 800° to 1,200° C. However, when the calcining temperature exceeds 1,200° C., the silica carrier suffers from remarkable crystallization, which undesirably leads to deteriorated catalytic activity of the catalyst supported on the carrier.

The catalyst used in the process of the present invention exhibits considerably enhanced selectivity of the desired cycloolefin as compared with the catalyst containing ruthenium alone or the conventional catalyst composed of co-supported components. The reason why the improved selectivity of cycloolefin is obtained using the catalyst of the present invention is not clearly appreciated. However, it is assumed that the improvement of the selectivity of cycloolefin is caused by active sites useful for production of cycloolefin, which are formed by interactions between ruthenium and the metal of the second component, between ruthenium and the metal of the third component, between the metal of the second component and the metal of the third component, and in the case of using the carrier, between the carrier and the respective catalytically active metal components.

The above-mentioned catalyst used in the process of the present invention may be prepared according to any conventionally known method for production of a general metal catalyst. The starting materials suitably used for preparation of the respective catalytically active metal components constituting the catalyst, include, for example, metal halides, metal nitrates, metal acetates, metal sulfates or complex compounds containing the respective metals. In the event that the catalyst is used in the form of non-carrier type catalyst, the catalyst is prepared by the following method. Namely, a mixture solution containing ruthenium and desired co-catalyst metal components (second and third metal components) is subjected to a known co-precipitation method such as an alkali precipitation method or to a distilling and drying process, thereby obtaining a solidified product as a precursor of the catalyst.

In the event that the catalyst is used in the form of a carrier-supported type catalyst, the catalyst can be prepared by the following method. Namely, first, the precursor of the catalyst is prepared in the same manner as described above. The co-supported metal components of ruthenium, i.e., the second and third metal components can be supported on the carrier simultaneously with ruthenium. Alternatively, the co-supported metal components may be supported on the carrier after ruthenium is supported on the carrier. Also, ruthenium may be supported on the carrier on which the second and third co-supported components are already supported.

The suitable method for supporting the catalytically active metal components on the carrier include a distilling and drying method in which the carrier is immersed in a solution containing the active components and then a solvent is distilled while stirring, thereby solidifying the active components; a spraying method in which a solution containing the catalytically active components is sprayed while maintaining the carrier in a dried state; or an impregnation-supporting method in which the carrier is immersed in the solution containing the catalytically active components and then the solution is subjected to a filtration. Examples of the suitable solvent used upon supporting the catalytically active components on the carrier includes, for example, water or an organic solvent such as alcohol, acetone, tetrahydrofuran, hexane, toluene and the like.

The thus prepared precursor of the catalyst, which contains ruthenium and the co-supported metal components, is reduced to obtain an activated catalyst. The reducing method includes a catalytic reduction method in which a hydrogen gas is used as a reducing agent, or a chemical reduction method in which formalin, boron sodium hydride, hydrazine or the like is used as a reducing agent. Among them, the catalytic reduction method using a hydrogen gas is preferred. In the catalytic reduction method, the reduction reaction may be carried out at a temperature of generally from 80° to 500° C., preferably from 100° to 450° C. When the temperature is less than 80° C., the reduction percentage is considerably deteriorated. On the other hand, when the temperature exceeds 500° C., sintering of ruthenium particles is likely to occur, resulting in a low yield and a low selectivity of cycloolefin.

The reaction system of the present invention necessitates the presence of water. An amount of water used in the reaction system is in the range of generally 0.1 to 20 parts by weight, preferably 0.5 to 10 parts by weight based on one part by weight of monocyclic aromatic hydrocarbon. Under such conditions as mentioned above, the resultant mixture is divided into two liquid phases composed of a first organic liquid phase (oil phase) containing mainly the remainder of the starting materials and the reaction product, and a second liquid phase (water phase) containing water. In the case where a ratio of the oil phase to the water phase or vice versa is too large, it is difficult to clearly distinguish the two phases from each other, so that separation of the two phases cannot be performed. Moreover, if an amount of water used is too large or too small, the effect of water cannot be exhibited to a sufficient extent. In addition, if too much water is used, it is necessary to make the reaction vessel undesirably large.

In the reaction system of the present invention, the metal salts may be used in combination. Examples of suitable metal salts usable in the reaction system of the present invention, may include a salt of metal elements belonging to Group I of the Periodic Table, such as lithium, sodium or potassium, a salt of metal elements belonging to Group II of the Periodic Table, such as magnesium or calcium, (The group numbers are based on IUPAC nomenclature of inorganic chemistry, revised edition (1989)), or a nitrate, a chloride, a sulfate, a acetate or a phosphate of zinc, manganese, cobalt or the like. Especially, examples of the preferred metal salts include zinc sulfate and cobalt sulfate. An amount of the metal salt used is in the range of generally from $1 \times 10^{-5}$ to 1 part by weight, preferably from $1 \times 10^{-4}$ to 0.1 part by weight based on one part by weight of water.

Further, the above-mentioned catalyst of the present invention can exhibit a high reaction yield even without adding of the additives such as the above-mentioned metal salts. Generally, in the reaction system in which the additives such as the metal salts are contained, there occurs a tendency that a catalytic activity per a unit weight of ruthenium is considerably deteriorated. On the other hand, in the reaction system in which the catalyst according to the present invention which contains no additive is used, there is a tendency that the catalytic activity is maintained at a relatively high level. Furthermore, the reaction system containing no metal salt generally has a tendency that the selectivity of the partial hydrogenation reaction becomes slightly lowered, as compared with the resection system containing the metal salts as the additive. Nevertheless, the reaction system containing no metal salt shows an extremely high catalytic activity, simplified procedures and low corrosion to the reaction vessel, thereby producing the desired product in industrial quantities.

Examples of monocyclic aromatic hydrocarbon which is subjected to the partial hydrogenation reaction according to the present invention, may include benzene, toluene, xylene, or substituted benzene having an alkyl substituent group with 1 to 4 carbon atoms. The reaction temperature used in the reaction system is generally in the range of 50° to 250° C., preferably 100° to 220° C. When the reaction temperature exceeds 250° C., the selectivity of producing the desired cycloolefin decreases. On the other hand, when the reaction temperature is less than 50° C., the reaction rate decreases considerably. The reaction pressure used in the reaction system is in the range of 0.1 to 20 MPa, preferably 0.5 to 10 MPa. If the reaction pressure exceeds 20 MPa, it is disadvantageous from an industrial standpoint. On the other hand, when the reaction pressure is less than 0.1 MPa, the reaction rate decreases considerably, which becomes uneconomic in view of the facilities used. The partial hydrogenation reaction according to the present invention can be conducted in the form of a gas phase reaction or a liquid phase reaction. Preferably, the reaction of the present invention is carried out in a liquid phase. The partial hydrogenation reaction of the present invention can be carried out in either a batch or continuous manner using one or two reaction vessels, though it is not particularly restricted. Further, the partial hydrogenation reaction of the present invention can be performed such that monocyclic aromatic hydrocarbon, water and catalytically active components are suspended together to form a liquid reaction mixture and then a hydrogen gas is introduced into the liquid reaction mixture. At this time, the hydrogen gas is supplied into the liquid reaction mixture generally through a nozzle.

In accordance with the present invention, cycloolefin production can be carried out with high selectivity by a partial hydrogenation reaction of monocyclic aromatic hydrocarbon in which a catalyst having a high activity is used. In addition, cycloolefin can be also produced under conditions in which attrition or deterioration of the reaction vessel and the catalyst are unlikely to occur.

EXAMPLES

The present invention is described in more detail by way of examples which are not intended to constitute a definition or limitation of the present invention.

As used herein, "wt %" appearing through the examples and comparative examples means "percentage by weight." Further, conversion percentage and selectivity appearing in the examples and comparative examples are:

(1) Conversion percentage (%)=(number of moles of MAH consumed during the reaction)/ (number of moles of MAH supplied into the reaction system)×100
(wherein MAH represents "monocyclic aromatic hydrocarbon".)

(2) Selectivity (%)=(number of moles of CyO produced)/ (number of moles of MAH consumed during the reaction) ×100
wherein MAH represents the same meaning as above and CyO represents "cycloolefin."

Example 1

0.87 g of zirconium oxynitrate dehydrate was dissolved in 20 ml of pure water to obtain an aqueous solution. 8.0 g of Silica (Trade Name: CARIACT 50, manufactured by Fuji Silicia Kagaku CO., LTD.) was added to the aqueous solution. After immersing the silica in the aqueous solution at room temperature, water was removed from the mixture by distillation to obtain a dried product. Next, the dried product was calcined at a temperature of 1000° C. for 4 hours under an air-stream. As a result, the silica carrier was prepared, which was modified with 5% by weight of zirconia based on silica. The thus obtained silica carrier was subjected to an analysis to determine a pore volume of the silica carrier. The pore volume of the pores having a pore radius of 20 to 100,000 Å was 1.35 ml/g. The pore volume of the pores having a pore radius of 20 to 100 Å was 0.069 ml/g and the percentage of the pore volume of the pores having a pore radius of 20 to 100 Å to an entire pore volume of the carrier is 5.1%.

The zirconium-modified silica carrier obtained above was added to an aqueous solution containing a predetermined amount of ruthenium chloride, zinc chloride and chlorogold acid. After the zirconium-modified silica carrier was immersed in the aqueous solution at a temperature of 60° C. for one hour, water was removed from the resultant mixture by distillation to obtain a dried product. It was confirmed that the thus obtained dried product was composed of the silica carrier and the catalyst containing ruthenium (Ru), zinc (Zn) and gold (Au) (as the catalytically active components) supported on the silica carrier, and each of the catalytically active components were contained therein in an amount of 0.5% by weight based on the silica carrier. A reduction of the catalyst was carried out at a temperature of 200° C. for three hours under a hydrogen gas stream to activate the respective catalytically active components of the catalyst.

An autoclave having a internal volume of 500 ml and made of stainless steel (SUS-316) was charged with 150 ml of water, 1.0 g of the catalyst (including a carrier) obtained above and 100 ml of benzene. Further, a hydrogen gas was supplied into the autoclave in a flow rate of 150 Nl per hour while maintaining the interior of the autoclave at a temperature of 150° C. and a pressure of 50 MPa. The reaction mixture was then stirred while rotating the mixture at 1000 rpm, thereby subjecting benzene to partial hydrogenation reaction. The resulting reaction product was removed at appropriate intervals through a nozzle mounted to the reaction vessel. An oil phase of the reaction product was analyzed by using a gas chromatography. The results of the analysis are shown in Table 1. The selectivity of cyclohexene was evaluated at the time when the conversion percentage of benzene reached about 20%.

Example 2

The same procedure as in Example 1 was conducted except that the catalyst, which contained ruthenium (Ru), zinc (Zn) and gold (Au) in amounts of 0.5% by weight, 0.5% by weight and 2.0% by weight, respectively, based on the silica carrier, was used instead of the catalyst used in Example 1. The results are also shown in Table 1.

Comparative Example 1

The same procedure as in Example 1 was conducted except that the catalyst, which had no gold content and contained ruthenium in an amount of 0.5% by weight and zinc in an amount of 0.5% by weight, based on the silica carrier, was used instead of the catalyst used in Example 1. The results are also shown in Table 1.

TABLE 1

| Example Nos. | Catalyst Element | Amount (wt %) | Time (min.) | Conversion percentage of Benzene (%) | Selectivity of Cyclohexene (%) |
|---|---|---|---|---|---|
| Example 1 | Ru | 0.5 | 10 | 21.5 | 54.0 |
|  | Zn | 0.5 |  |  |  |
|  | Au | 0.5 |  |  |  |
| Example 2 | Ru | 0.5 | 12 | 20.1 | 60.4 |
|  | Zn | 0.5 |  |  |  |
|  | Au | 2.0 |  |  |  |
| Comp. Exam. 1 | Ru | 0.5 | 7 | 21.0 | 49.1 |
|  | Zn | 0.5 |  |  |  |

Example 3

An autoclave having an internal volume of 500 ml and made of titanium was charged with 150 ml of water, 18 g of zinc sulfate hepta-hydrate, 3.75 g of the catalyst prepared in Example 1 and 100 ml of benzene. Then, a hydrogen gas was supplied into the autoclave in a flow rate of 57 Nl per one hour while maintaining the interior of the autoclave at a temperature of 150° C. and a pressure of 50 MPa. The reaction mixture was compulsively stirred while rotating the mixture at 1000 rpm, thereby subjecting benzene to partial hydrogenation reaction. The resulting reaction product was removed at appropriate intervals through a nozzle mounted to the reaction vessel. The oil phase of the reaction product was analyzed by using a gas chromatography. The results are shown in Table 2. Incidentally, the selectivity of cyclohexene was evaluated at the time when the conversion percentage of benzene reached about 30% and about 60%.

Example 4

The same procedure as in Example 3 was conducted except that the content of gold (Au) in the catalyst was changed to 0.1% by weight as shown in Table 2. The results are also shown in Table 2.

Comparative Example 2

The same procedure as in Example 3 was conducted except that the catalyst of Comparative Example 1 was used instead of the catalyst of Example 3. The results are also shown in Table 2.

Comparative Example 3

The same procedure as in Example 3 was conducted except that the catalyst, which had no zinc content and contained ruthenium in an amount of 0.5% by weight and gold in an amount of 0.5% by weight, was used instead of the catalyst used in Example 3. The results are also shown in Table 2.

Comparative Example 4

A catalyst containing ruthenium (Ru), cobalt (Co) and copper (Cu) in an amount of 0.5% by weight, 0.5% by weight and 0.05% by weight, respectively, was prepared in the same manner as described in Example 1. In the preparation of the catalyst, cobalt nitrate and copper nitrate were used as starting materials for the respective cobalt and copper components. Then, the same procedure as in Example 3 was conducted except that the catalyst prepared above was used instead of the catalyst used in Example 3. The results are also shown in Table 2. The selectivity of cyclohexene was evaluated at the time when the conversion percentage of benzene reached about 30% and about 60%.

Comparative Example 5

The same procedure as in Example 3 was conducted except that the catalyst, which had no copper content and contained ruthenium (Ru) in an amount of 0.5% by weight and cobalt (Co) in an amount of 0.5% by weight instead of that used in Example 3. The results are also shown in Table 2.

TABLE 2

| Example Nos. | Catalyst Element | Amount (wt %) | Time (min.) | Conversion percentage of Benzene (%) | Selectivity of Cyclo- hexene (%) |
|---|---|---|---|---|---|
| Example 3 | Ru | 0.5 | 40 | 30.0 | 86.1* |
| | Zn | 0.5 | 100 | 60.5 | 75.7** |
| | Au | 0.5 | | | |
| Example 4 | Ru | 0.5 | 90 | 57.4 | 75.3** |
| | Zn | 0.5 | | | |
| | Au | 0.1 | | | |
| Comp. Exam. 2 | Ru | 0.5 | 40 | 36.1 | 79.5* |
| | Zn | 0.5 | | | |
| Comp. Exam. 3 | Ru | 0.5 | 35 | 29.3 | 78.1* |
| | Au | 0.5 | | | |
| Comp. Exam. 4 | Ru | 0.5 | 49 | 29.3 | 83.2* |
| | Co | 0.5 | | | |
| | Cu | 0.05 | 155 | 57.2 | 71.5** |
| Comp. Exam. 5 | Ru | 0.5 | 41 | 29.1 | 76.2* |
| | Co | 0.5 | | | |

(Note)
*Selectivity of cyclohexene when the conversion percentage of Benzene was about 30%.
**Selectivity of cyclohexene when the conversion percentage of Benzene was about 60%.

Example 5

The catalyst was prepared in the same manner as in Example 1 except that zirconium silicate was used as a carrier instead of silica. Then, the same procedure as in Example 3 was conducted except that the catalyst prepared above was used instead of that of Example 3. The results are shown in Table 3.

Comparative Example 6

The same procedure as in Example 5 was conducted except that the catalyst had no gold content and contained ruthenium (Ru) in an amount of 0.5% by weight and zinc (Zn) in an amount of 0.5% by weight instead of that used in Example 5. The results are shown in Table 3.

TABLE 3

| Example Nos. | Catalyst Element | Amount (wt %) | Time (min.) | Conversion percentage of Benzene (%) | Selectivity of Cyclo- hexene (%) |
|---|---|---|---|---|---|
| Example 5 | Ru | 0.5 | 30 | 30.3 | 84.4 |
| | Zn | 0.5 | | | |
| | Au | 0.5 | | | |
| Comp. Exam. 6 | Ru | 0.5 | 27 | 31.0 | 79.5 |
| | Zn | 0.5 | | | |

What is claimed is:

1. A process of producing a cycloolefin comprising contacting a catalyst and partially hydrogenating under effective hydrogenation conditions a monocyclic aromatic hydrocarbon in the presence of water 0.1 to 20 parts by weight of monocyclic aromatic hydrocarbon at a temperature in the range of 50° to 250° C. and a reaction pressure in the range of 0.1 to 10 MPa to produce a cycloolefin, wherein said catalyst is a ternary catalyst containing (a) ruthenium, (b) zinc and (c) at least one selected from the group consisting of gold, silver and copper the atomic ratio of zinc to ruthenium is in the range of 0.01 to 20 and the atomic ratio of ruthenium to said at least one element selected from the group consisting of gold, silver and copper is in the range of 0.01 to 20.

2. The process according to claim 1, wherein said catalyst is a ternary catalyst containing ruthenium, zinc and gold.

3. The process according to claim 1, wherein said catalyst is a ternary catalyst containing ruthenium, zinc and silver.

4. The process according to claim 1, wherein said catalyst is a ternary catalyst containing ruthenium, zinc and copper.

5. The process according to claim 1, wherein an atomic ratio of zinc to ruthenium in said ternary catalyst is in the range of 0.05 to 10.

6. The process according to claim 1, wherein an atomic ratio of ruthenium to at least one element selected from the group consisting of gold, silver and copper in said ternary catalyst is in the range of 0.03 to 10.

7. The process according to claim 1, wherein said ternary catalyst is supported on a carrier.

8. The process according to claim 7, wherein an amount of said ternary catalyst supported on said carrier is in the range of 0.001 to 10% by weight based on a total amount of said ternary catalyst and said carrier.

9. The process according to claim 7, wherein an amount of said ternary catalyst supported on said carrier is in the range of 0.05 to 5% by weight based on a total amount of said ternary catalyst and said carrier.

10. The process according to claim 7, wherein said carrier has a pore volume of pores having a pore radius of 20 to 100,000 Å is in the range of 0.3 to 10 ml/g and a percentage of a pore volume of pores having a pore radius of 20 to 100 Å to an entire pore volume of said carrier is not more than 15%.

11. The process according to claim 7, wherein said carrier is an oxide carrier.

12. The process according to claim 11, wherein said oxide carrier contains silica.

13. The process according to claim 11, wherein said oxide carrier contains zirconium.

14. The process according to claim 11, wherein said oxide carrier is zirconium silicate.

15. The process according to claim 1, wherein said monocyclic aromatic hydrocarbon is benzene.

16. The process according to claim 1, wherein said partial hydrogenation is carried out in the presence of a metal salt.

17. The process according to claim 16, wherein an amount of said metal salt is from $1 \times 10^{-5}$ to 1 part by weight based on one part by weight of water in the reaction system.

* * * * *